United States Patent [19]

Klemann et al.

[11] Patent Number: 4,927,659

[45] Date of Patent: May 22, 1990

[54] TRIS-HYDROXYMETHYL LOWER ALKANE ESTERS AS FAT MIMETICS

[75] Inventors: Lawrence P. Klemann, Somerville; John W. Finley, Whippany; Anthony Scimone, Cedar Grove, all of N.J.

[73] Assignee: Nabisco Brands, Inc., East Hanover, N.J.

[21] Appl. No.: 312,076

[22] Filed: Feb. 16, 1989

[51] Int. Cl.$^5$ .......................... A23D 5/00; C11C 3/00
[52] U.S. Cl. ..................... 426/611; 426/601; 426/566; 426/804; 260/410.6; 560/198
[58] Field of Search ............... 426/566, 611, 601, 804; 260/410.6; 560/198

[56] References Cited

U.S. PATENT DOCUMENTS

| | | |
|---|---|---|
| 519,980 | 5/1894 | Winter . |
| 2,924,528 | 2/1960 | Barsky et al. . |
| 2,962,419 | 11/1960 | Minich ................................ 167/81 |
| 2,993,063 | 7/1961 | Alsop et al. ...................... 260/410.6 |
| 3,495,010 | 2/1970 | Fossel ................................ 424/312 |
| 3,579,548 | 5/1971 | Whyte ............................. 260/410.7 |
| 3,600,186 | 8/1971 | Mattson .................................. 99/1 |
| 3,637,774 | 1/1972 | Babayan et al. ................. 260/410.6 |
| 3,818,089 | 6/1974 | Bayley et al. ............................ 424/9 |
| 3,876,794 | 4/1975 | Rennhard ............................ 426/152 |
| 4,005,195 | 1/1977 | Jandacek ............................ 424/180 |
| 4,304,768 | 12/1981 | Staub et al. ........................ 424/180 |
| 4,508,746 | 4/1985 | Hamm ................................. 426/601 |
| 4,631,196 | 12/1986 | Zeller ................................. 426/580 |
| 4,797,300 | 1/1989 | Jandacek et al. ................... 426/549 |

FOREIGN PATENT DOCUMENTS

| | | |
|---|---|---|
| 1106681 | 8/1981 | Canada ................................. 99/156 |
| 0205273 | 12/1986 | European Pat. Off. . |
| 0233856 | 8/1987 | European Pat. Off. . |
| 0254547 | 1/1988 | European Pat. Off. . |
| 3529564 | 3/1987 | Fed. Rep. of Germany . |
| 207070 | 2/1984 | German Democratic Rep. . |

OTHER PUBLICATIONS

Altschul, M., Low Calorie Foods, 43 Food Tech., pp. 1-13, (1989).
Borgstrom, B., Lipases, Elsevier, p. V, (1984).
LaBarge, R. G., A Search for a Low Caloric Oil, 42 Food Tech., 84-90, (1988).
Mattson, F. H., and Nolen, G. A., Absorbability by Rots of Compounds, 102, J. Nutr. 1171-1176, (1972).
Mattson, F. H., and Volpenhein, R. A., Hydroylsis of Fully Esterified Alcohols, 13 J. Lip. Res., 325-328, (1972).
Mattson, F. H., and Volpenhein, R. A., Rate and Extent of the Absorption of Fatty Acids, 102 J. Nutr., 1177-1180, (1972).
Mattson, F. H. and Volpenhein, R. A., Digestion in Vitro of Ergthritol Esters, 13 J. Lip. Res., 777-782, (1972).
Ponomareff-Baumann, M., et al., Fat Homologues, 43 Pharm. Acta Helv., 158-176, (1967), (German and Translation).
Barnes and Fainman, 13 Lub Eng, 454–458, (1957).
Bell et al., 53 JAOCS, 511-517, (1976).
Booth and Gros, 40 JAOCS, 551-553, (1963).
Goodman and Gilman, 7th ed., 1985, pp. 1002-1003.
Halliburton et al., 13 J B C 301-305, (1919).
Hamm, 49 J. Food Sci 419-428, (1984).
Haumann, 63 JAOCS 278-287, (1986).
Lapworth and Pearson, 13 J B C 296-300, (1919).

Primary Examiner—Donald E. Czaja
Assistant Examiner—Evan Federman

[57] ABSTRACT

Trishydroxymethyl ethane and propane, esterified with fatty acids, are physiologically compatible, partially digestible edible synthetic fat replacements for foods and pharmaceuticals.

48 Claims, No Drawings

TRIS-HYDROXYMETHYL LOWER ALKANE ESTERS AS FAT MIMETICS

BACKGROUND OF THE INVENTION

This invention relates to the use of trishydroxymethyl ethane and propane fatty acid esters as partially digestible edible synthetic fat replacements in foods and pharmaceuticals.

Since fats provide nine calories per gram compared to four calories per gram provided by protein or carbohydrates, major research efforts toward reduction of caloric intake for medical or health reasons have focused on ways to produce food substances that provide the same functional and organoleptic properties as fats, but not the calories.

A major strategy for developing low calorie replacement fats has been to structurally re-engineer natural triglycerides in such a way as to retain their conventional functional properties in foods, while removing their susceptibility toward hydrolysis or subsequent absorption during digestion. To this end, the the fatty acids attached to glycerol have been replaced with alternate acids (U.S. Pat. No. 3,579,548 to Whyte); groups have been inserted between the fatty acids and the glycerol backbone ("propoxylated glycerols", Eur. Pat. Ap. No. 254,547 to White and Pollard); the ester linkages have been replaced by ether linkages (U.S. Pat. No. 3,818,089 to Bayley and Carlson, and Can. Pat. No. 1,106,681 to Trost); the ester linkages have been reversed (U.S. Pat. No. 4,508,746 to Hamm); and the glycerol moeity has been replaced with an alternate alcohol (e.g., ethylene glycol in U.S. Pat. No. 2,924,528 to Barskey et al., and U.S. Pat. No. 2,993,063 to Alsop and Carr).

A second major approach to the development of a low calorie fat replacement has been to explore or synthesize nonabsorbable polymeric materials structurally unlike triglycerides, but having physical properties similar to edible fat. Mineral oil was disclosed as early as 1894 (U.S. Pat. No. 519,980 to Winter), and, more recently, polydextrose (U.S. Pat. No. 4,631,196 to Zeller), polyglucose and polymaltose (U.S. Pat. No. 3,876,794 to Rennhard), polysiloxane (Eur. Pat. Ap. No. 205,273 to Frye), jojoba wax (W. Ger. Pat. No. 3,529,564 to Anika), and polyethylene polymers (E. Ger. Pat. No. 207,070 to Mieth, et al.) have been suggested.

A third major strategy combines the first two. Rather than restructure triglyceride molecules or find a substitute structurally very dissimilar, this approach explores the use of various polyol esters, compounds which have numbers of fatty acid groups in excess of the three in conventional fat triglycerides, as nonabsorbable fat replacements. Fully esterified sugars were suggested as fat replacements during World War I (notably mannitol, Lapworth, A., and Pearson, L.K., and Halliburton, W.D., et al., 13 J. Biol. Chem. 296 and 301 (1919)), and the Southern and Western Regional Research Laboratories of the U.S.D.A. investigated the feasibility of using amylose esters as new-type fats during the 1960's (see Booth, A.N., and Gros, A.T., 40 J. Amer. Oil Chem. Soc. 551 (1963) and the references cited therein). More recently, sucrose polyesters have been suggested (U.S. Pat. No. 3,600,186 to Mattson and Volpenhein). The caloric availability and digestibility of a series of dimeric and polymeric glycerides including diglyceride esters of succinic, fumaric, and adipic acids, and polymeric fats from stearic, oleic and short-chain dibasic acids were assessed by the U.S.D.A. group cited supra, and polyglycerol esters have since been suggested (U.S. Pat. No. 3,637,774 to Babayan and Lehman).

Nondigestible or nonabsorbable triglyceride analogues, polyol esters, and polymeric materials have proved disappointing as fat replacements when tested in feeding trials, where gastrointestinal side effects occurred, in some cases so extreme that frank anal leakage was observed (for recent reviews, see Hamm, D.J., 49 J. Food Sci. 419 (1984) and Haumann, B.J., 63 J. Amer. Oil Chem. Soc. 278 (1986)). Nondigestible fats act as a laxative and are expelled from the body, eliciting foreign body reactions like those early documented for mineral oil (Goodman and Gilman's Pharmacological Basis of Therapeutics, 7th ed., Macmillan Pub. Co., N.Y. 1985, pp. 1002-1003). Polyglycerol and polyglycerol esters, for example, suggested as fat replacements supra, have been suggested for use as fecal softening agents as well (U.S. Pat. No. 3,495,010 to Fossel). A number of remedies have been recommended to combat the anal leakage observed when sucrose polyesters are ingested (e.g., employing cocoa butters, U.S. Pat. No. 4,005,195 to Jandacek, or incorporating saturated fatty groups, Eur. Pat. Ap. No. 233,856 to Bernhardt), and dietary fiber preparations have been incorporated into polysaccharide and/or polyol-containing foodstuffs to help inhibit the diarrheal effect (U.S. Pat. No. 4,304,768 to Staub et al.).

SUMMARY OF THE INVENTION

An object of the present invention is to provide a fat replacement more compatible with normal digestion. More particularly, it is an object of the present invention to provide a more digestible fat replacement which interferes less with fat metabolism, thus avoiding diarrhea and other laxative side effects. It is a further object of the present invention to provide a partially digestible fat replacement which may, if desired, be engineered to provide essential fatty acids.

In the practice of this invention, fatty acid esters trishydroxymethyl ethane and propane, are used as partially digestible edible fat replacements.

DETAILED DESCRIPTION OF THE INVENTION

Minich suggested neopentyl alcohol esters as fat substitutes in dietetic compositions (U.S. Pat. No. 2,962,419). He used pentaerythritol, a tetrahydric neopentyl sugar alcohol formed when pentaerythrose condensed from acetaldehyde and formaldehyde undergoes a crossed Cannizzaro reaction, in his examples. He tested pentaerythritol tetracaprylate in lipase assays, rat feeding studies, and food recipes, and concluded the esters, which "do not break down in the stomach or upper intestinal tract . . . may be used to control the intake of fat" (col. 1, lines 63-65). Long known to be useful as high temperature lubricants (see reviews by Barnes, R.S., and Fainman, M.Z., 13 Lub. Eng. 454 (1957), and Bell, E.W., et al., 53 J. Amer. Oil Chem. Soc. 511 (1976)), the family of compounds have since been often cited in patents and periodicals as examples of nondigestible triglyceride analogues which sterically hinder normal fat hydrolysis because of branching on the alcohol side of the triglyceride molecule.

The present invention is based on the surprising finding that trishydroxymethyl ethane and propane esters, which have three side chains rather than the four found in Minich's pentaerythritol esters, are not nondigestible. On the contrary, these trishydroxymethyl lower alkane esters are partially digestible. Slowly hydrolyzed by lipase in vitro, the esters exhibit, in in vivo feeding studies, a caloric availability qualitatively estimated as a third that of natural fat. Instead of passing through the digestive tract unchanged, eliciting the undesirable side effects of oral foreign nondigestible materials discussed above, these trishydroxymethyl alkane esters are a food.

The trishydroxymethyl ethane and propane esters of this invention comprise compounds having the following general formula:

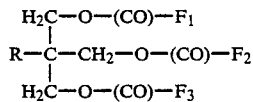

where R is a methyl ($CH_3$—) or ethyl ($CH_3CH_2$—) alkyl group, and $F_1$, $F_2$, and $F_3$ are fatty acid residues (fatty alphatic groups).

Thus, this invention comprises the fatty acid esters of the trishydroxymethyl alcohols trishydroxymethyl ethane and trishydroxymethyl propane.

The fatty acid residues, $F_1$, $F_2$, and $F_3$, esterified to trishydroxymethyl ethane and propane may be the same or different, and may comprise a mixture of residues. The term "fatty acids" used here means organic fatty acids containing a sufficient number of carbon atoms to provide for the physical properties commonly attributed to edible fats and oils. Fatty acids may be synthetic or natural, saturated or unsaturated, with straight or branched chains, and have from four to twenty-two carbon atoms, preferably from ten to twenty, and, most preferably, from twelve to eighteen carbon atoms. Examples of fatty acids are capric, undecanoic, lauric, myristic, palmitic, stearic, arachidic, behenic, oleic, linoleic, linolenic, eleostearic, and arachidonic acids. Mixtures of fatty acids may also be used, such as those obtained from non-hydrogenated or hydrogenated sunflower oil, safflower oil, soybean oil, olive oil, sesame oil, peanut oil, palm kernel oil, cottonseed oil, palm oil, babassu nut oil, canola oil, rice bran oil, or corn oil.

The trishydroxymethyl alkane esters may be incorporated into any food composition or use in conjunction with any edible material. The term "edible material" is broad and includes anything edible, whether or not intended for nutrition, e.g., it can be an additive for fats or oils, an antispatter agent, an emulsifier, or other minor functional ingredient. Thus, chewing gum, flavored coatings, oils and fats intended only for frying, and the like are included. In these, all or a portion of the usual fat is replaced by a compound of the invention.

Representative of edible materials which can contain the fat mimetic compounds of this invention in full or partial replacement of natural fat are: frozen desserts, e.g., sherbet, ice cream, ices, or milk shakes; puddings and pie fillings; margarine substitutes or blends; flavored bread or biscuit spreads; mayonnaise; salad dressing, both emulsified and non-emulsified; filled dairy products such as filled cream or filled milk; dairy or non-dairy cheese spreads; coffee lighteners, liquid and dried; flavored dips; frying fats and oils; reformed and comminuted meats; meat substitutes or extenders; whipped toppings; compound coatings; frostings and fillings; cocoa butter replacements or blends; candy, especially fatty candies such as those containing peanut butter or chocolate; chewing gum; bakery products, e.g., cakes, breads, rolls, pastries, cookies, biscuits, and savory crackers; mixes or ingredient premixes for any of these; as well as flavor, nutrient, drug or functional additive delivery systems.

The following is a list of representative, but not limiting, examples of trishydroxymethyl alkane esters of this invention:

1,1,1-Tris-hydroxymethylethane Trioleate (1)

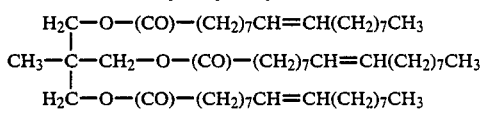

1,1,1-Tris-hydroxymethylethane Trimyristate (2)

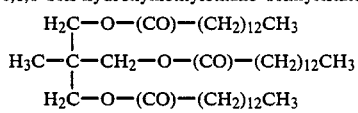

1,1,1-Tris-hydroxymethylethane Tri-10-undecenate (3)

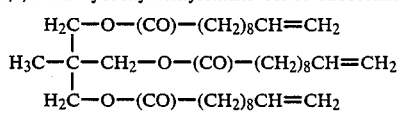

1,1,1-Tris-hydroxymethylethane Dioleate/Stearate (4)

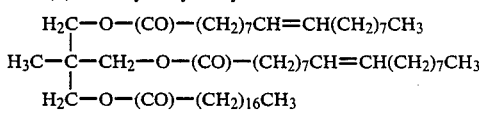

1,1,1-Tris-hydroxymethylethane Distearate/Oleate (5)

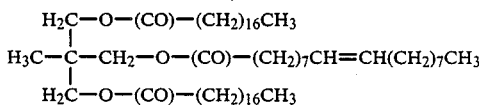

1,1,1-Tris-hydroxymethylpropane Trioleate (6)

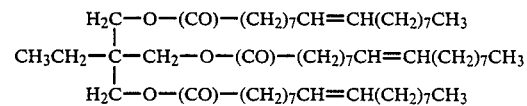

1,1,1-Tris-hydroxymethylpropane Tri-10-undecenate (7)

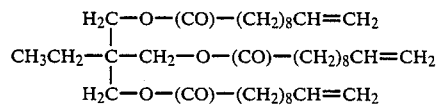

1,1,1-Tris-hydroxymethylpropane Tristearate (8)

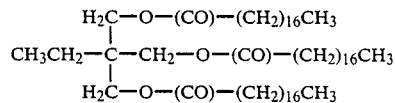

EXAMPLES

The following examples are presented to further illustrate and explain the present invention and should not be taken as limiting in any regard. Unless otherwise indicated, all parts and percentages are by weight, and are based on the weight at the particular stage of the processing being described. The proton NMR spectra have assigned chemical shifts, multiplicities, and intensities consistent with the structures with which they are reported.

EXAMPLE 1

1,1,1-Tris-hydroxymethylethane trioleate (also called 1,1,1-tris(oleoyloxymethyl)ethane), a tris-hydroxymethyl lower alkane ester of this invention, is synthesized in this example.

1,1,1-Tris(hydroxymethyl)ethane (12 g., 0.1 mole) is dissolved in 150 mL tetrahydrofuran (THF) by warming, and to the solution is added 91 g. (0.3 mole) of technical grade oleoyl chloride. When gas evolution subsides, vacuum ($-100$ torr) is applied for 15 minutes, then the reaction mixture is allowed to stand at ambient temperature and pressure for 16 hours. Evaporation of solvent and filtration of the residue through silica (using 1500 mL hexane) affords 65 g. (71%) of crude product as a yellow oil.

Proton NMR spectrum in $CDCl_3$: chemical shift in ppm (multliplicity, intensity, assignment): 5.35 (multiplet, 6 H, HC=CH), 4.01(singlet, 6 H, O—$CH_2$), 2.31 (triplet, 6 H, O=C—$CH_2$), 2.02, 1.61 and 1.29 (multiplets, 72 H, —$CH_2$—), 1.01 (singlet, 3 H, —$CH_3$) and 0.87 (triplet, 9 H, —$CH_3$).

Analysis: Calculated for $C_{59}H_{108}O_6$, FW 913.50: C 7.57, H 11.92, O 10.51%; Found: C 77.45, H 11.85%.

EXAMPLE 2

1,1,1-Tris-hydroxymethylethane distearate/oleate, a one-to-three adduct of tris-hydroxymethylethane having a 2:1 ratio of stearic to oleic acids, a tris-hydroxymethyl alkane mixed ester of this invention, is synthesized in this example.

A combination of one equivalent tris-hydroxymethyl ethane with two equivalents stearoyl chloride and one equivalent oleoyl chloride in pyridine affords an oil.

Proton NMR analysis shows a 1.75/1.25 ratio of saturated to unsaturated fatty acid moieties in the product.

EXAMPLE 3

1,1,1-Tris-hydroxyethane dioleate/stearate, a one-to-three adduct of tris-hydroxymethyl ethane and a 2:1 ratio of oleic to stearic acids, another mixed trishydroxymethyl alkane ester of this invention, is prepared in this example.

A combination of one equivalent trishydroxymethyl ethane with one equivalent stearoyl chloride and two equivalents oleoyl chloride in pyridine affords an oil.

Proton NMR analysis shows a 0.86/2.14 ratio of saturated to unsaturated fatty acid moieties in the product.

EXAMPLE 4

1,1,1-Tris-hydroxymethylpropane trioleate (also called 1,1,1-tris(oleoyloxymethyl)propane), another trishydroxymethyl lower alkane ester of this invention, is synthesized in this example.

A solution of 1,1,1-tris(hydroxymethyl)propane (1.34 g., 0.01 mole), oleoyl chloride (10 mL, c. 0.03 mole) and 15 mL pyridine is shaken overnight at ambient temperature, then filtered through a short bed of silica gel. The filtrate is concentrated on the rotary evaporator to give an oil.

Proton NMR spectrum in $CDCl_3$: chemical shift in ppm (multliplicity, intensity, assignment): 5.35 (multiplet, 6 H, HC=CH), 4.01 (singlet, 6 H, $CH_2$—O), 2.30 (triplet, 6 H, $O_2C$—$CH_2$), 2.01 (broad multiplet, 12 H, C=C—$CH_2$), 1 60 (multiplet, 6 H, $O_2C$—C—$CH_2$), 1.47 (quartet, 2 H, propane $CH_2$), 1.30 (multiplet, 60 H, $CH_2$), and 0.87–0.88 (superimposed triplets, 12 H, $CH_3$).

EXAMPLE 5

1,1,1-Trishydroxymethylethane tri-10-undecenate (also called 1,1,1-tris(10-undecenoyloxymethyl)ethane), another trishydroxymethyl lower alkane ester of this invention, is synthesized in this example. To a solution of 1.2 g. (0.01 mole) 1,1,1-tris(hydroxymethyl)ethane in 10 mL pyridine is added 6.5 mL (c. 0.03 mole) 10-undecenoyl chloride. The mixture is shaken overnight at ambient temperature, filtered through silica (eluted with pentane), and the eluate concentrated to afford an oil. Proton NMR spectrum in $CDCl_3$: chemical shift in ppm (multliplicity, intensity, assignment): 5.78 (multiplet, 3 H, HC=C), 4.95 (multiplet, 6 H, C=$CH_2$), 3.97 (singlet, 6 H, $CH_2$—O), 2.29 (triplet, 6 H, O=C—$CH_2$), 2.01 (quartet, 6 H, C=C—$CH_2$), 1.59 (apparent quintet, 6 H, O=C—C—$CH_2$), 1.30 (multiplet, 30 H, $CH_2$) and 0.99 (singlet, 3 H, ethane —$CH_3$).

EXAMPLE 6

1,1,1-Trishydroxymethyl tri-10-undecenate (also called 1,1,1-tris(10-undecenoyloxymethyl)propane), another trishydroxymethyl lower alkane ester of this invention, is prepared in this example.

To a solution of 1.34 g. (0.01 mole) 1,1,1-tris (hydroxymethyl)propane in 10 mL pyridine is added 6.5 mL (c. 0.03 mole) 10-undecenoyl chloride. The mixture is shaken overnight at ambient temperature and filtered through silica (eluted with pentane). Concentration of the eluate affords an oil.

Proton NMR spectrum in $CDCl_3$: chemical shift in ppm (multliplicity, intensity, assignment): 5.81 (multiplet, 3 H, C=CH), 4.95 (multiplet, 6 H, C=$CH_2$), 4.01 (singlet, 6 H, $CH_2$—O), 2.29 (triplet, 6 H, $CH_2$—$CO_2$), 2.02 (apparent quartet, 6 H, C=C—$CH_2$), 1.60 (multiplet, 6 H, $CH_2$—C—$CO_2$), 1.48 (quartet, 2 H, propane $CH_2$), 1.30 (multiplet, 30 H, $CH_2$) and 0.87 (triplet, 3 H, $CH_3$).

EXAMPLE 7

1,1,1-Tris-hydroxymethylethane trimyristate (also called 1,1,1-tris(tetradecanoyloxymethyl)ethane), another trishydroxymethyl lower alkane ester of this invention, is prepared in this example.

A solution of tris(hydroxymethyl)ethane (1.20 g., 0.01 mole), myristoyl chloride (7.38 g., 0.03 mole) and pyridine (25 mL) is shaken at ambient temperature overnight. The reaction mixture is filtered, concentrated and refiltered through silica gel to afford an oil.

EXAMPLE 8

1,1,1-Tris-hydroxymethyl ethane trimyristate (also called 1,1,1-tris(myristoyloxymethyl) ethane) is prepared in an alternate procedure in this example.

Myristoyl chloride (1000 g., 4.05 mole) is charged to a 2-liter flask equipped with a magnetic stirrer bar, thermometer, and a gas outlet which is attached to a vacuum source by means of an acid trap (containing 500 g. solid NaOH pellets). With stirring, 160 g. (1.33 mole) 1,1,1-tris (hydroxymethyl)ethane is added and the slurry is placed under reduced pressure ($-100$ torr) and is warmed by means of a heating mantle. Between 40° and 80° C. gas (HCl) evolves vigorously from the reaction flask, and vacuum may need to be interrupted momentarily to avoid reactant carry-over. As gas evolution subsides, the temperature is raised to 120° C. ($-100$ torr), and these conditions are maintained until gas evolution is complete. Stirring under vacuum is continued for one hour, and the temperature is allowed to fall to about 80° C., vacuum is released, and the crude product is passed through a falling film still (conditions: 168° C., 0.8 Torr) to remove excess fatty acid residues.

The product oil is steam deodorized (conditions: 6 wt. % steam, 195–205° C., ca. 0.5 torr). Upon cooling, the colorless oil affords a white solid with a melting point of 36–40° C. The yield is quantitative. The titratable acidity (expressed as myristic acid) is less than 0.4 wt. %.

EXAMPLE 9

This example outlines the procedure for estimating the in vitro digestibility of the synthetic fat mimetics of this invention.

Preparation of Reaqents and Materials:

1. Buffer: A pH 7.1 phosphate buffer is prepared by dissolving 6.8 g. $KH_2PO_4$ in 1 L. of millipore filtered water (to yield 0.05 M phosphate). Fifty mg. $Ca(NO_3)_2$ and 5.0 g. cholic acid (Na salt, an ox bile isolate from Sigma) are added to give 300 microM $Ca^{++}$ and 0.5 % cholic acid in 0.05 M phosphate. The pH is adjusted to approximately 7.1 with solid NaOH. Several drops of Baker "Resi-analyzed" toluene are added to prevent bacterial growth during storage at 3–5° C.

2. Lipase: About 15 mg./mL commercial porcine pancreatic lipase from U.S. Biochemical Corporation is dissolved in buffer.

3. Substrates and Standards: A 1.0 mL volumetric flask is charged with an amount of lipid substrate (test substance or standard) calculated to give a concentration of 200 nanomoles per microliter in Baker "Resi-analyzed" toluene. (The proper concentration may be approximated by doubling the molecular weight of the lipid in question, dividing by 10, and diluting to the mark; this yields about 200 nanomoles per microliter.) This preparation affords the substrate to be used in the hydrolysis reactions.

Fatty acids and glyceride standards from Nu Chek or Sigma are prepared for elution on TLC plates (prewashed with 1:1 chloroform/methanol) by diluting the substrate solution with 10:1 toluene (1 part substrate plus 9 parts toluene) in septum vials.

Procedure:

In a 25 mL Erlenmeyer, emulsify 20 mL buffer and 40 microliters of substrate using an ultrasonic disrupter at a microtip maximum setting for approximately 10 seconds. This results in a 0.4 microliter/milliliter emulsion. Place in a 37° C. water bath and stir vigorously. After temperature equilibration, add 40 microliters of enzyme solution and start timing. Remove 5.0 mL aliquots at convenient time intervals for analysis. To establish a standard curve for triolein, aliquots are taken at 10, 20, 30 and 40 minutes. A zero time control should be run for all test compounds.

Add the aliquot to a 15 mL glass centrifuge tube containing a drop of concentrated HCl. Add approximately 3 mL of a 2:1 mixture of $CHCl_3:CH_3OH$ and shake vigorously. Centrifuge at approximately 5000 rpm for 5 minutes and transfer the bottom layer with a Pasteur pipet to a 5 mL septum vial. Repeat the extraction step once and combine the two bottom layers. Evaporate the solvent in nitrogen gas. After about half of the solvent is removed, add an equivalent volume absolute ethanol and continue evaporation in a nitrogen stream until dryness is achieved. Samples may be warmed with a heat gun to facilitate drying.

When the samples are dry, add exactly 200 microliters of toluene containing 10% DMSO, cap tightly, and spot TLC plate with 2.0 microliters per channel. (If 100% extraction efficiency of a zero time control, this amounts to 20 nanomoles of substrate spotted on the plate.) Develop with a suitable solvent system, for example, hexane: ethyl ether: acetic acid in a ratio of 60:40:1. After 15 cm elution, dry plate with a heat gun and determine amounts of starting substrate and products of hydrolysis by scanning 10 to 20 nanomoles per channel at a wavelength of 190 nm using the CAMAG TLC Scanner II densitometer equipped with a Spectra Physics 4270 integrator and comparing with controls run at the same time.

Results:

Using this procedure with the 1,1,1-tris-hydroxymethyl ethane trioleate prepared in Example 1, limited hydrolysis is observed after three hours contact with pancreatic lipase. Using a triglyceride control, triolein is substantially hydrolyzed in 10 minutes with this enzyme system.

EXAMPLE 10

This example illustrates how the novel fat mimetics of this invention are screened for caloric availability by a carefully controlled in vivo animal feeding study.

An experimental relationship between total calories ingested and animal body weight gain is established by monitoring the body weight gain associated with consumption of a nutritionally balanced diet containing varying concentrations of a reference substance such as corn oil which has a known caloric availability. Correlations between total calories ingested and body weight gain are excellent ($r=0.99$).

Caloric availability of an unknown substance is evaluated by substituting a specific weight of the unknown substance for the reference substance and observing the body weight gain. The gain in body weight is equated to a total number of calories using the correlation previously established for the reference data. The estimated number of calories ingested are divided by the weight of unknown substance to give the apparent calories per gram for the unknown substance. Generally speaking, in these bioavailability studies, the degree of perianal pelt soiling correlates with reduced bioavailability.

The test animals are six-week-old male Sprague-Dawley rats obtained from the Portage, Mich. facility of the Charles River Laboratories, Inc. After acclimation for 15 days, the test duration is 14 days. The dietary requirements are established by observing the actual feed consumption of animals provided with unlimited feed. All diets are prepared to contain 50% of the established dietary requirements plus any supplements of reference or unknown substances. In all tests so designed the test animals are maintained in very good health.

The test feeds are AIN-76A and fortified AIN-76A (hereinafter abbreviated "fort") AIN-76A (Teklad). The major components of these diets are as follows:

| component | AIN-76A | fortified AIN-76A |
|---|---|---|
| casein | 20% | 40% |
| corn starch | 15 | 8.08 |
| sucrose | 50 | 26.02 |
| fiber | 5 | 5 |
| corn oil | 5 | 5 |
| AIN mineral mix | 3.5 | 7 |
| AIN vitamin mix | 1 | 2 |

| component | AIN-76A | fortified AIN-76A |
|---|---|---|
| choline | 0.2 | 0.4 |
| methionine | 0.3 | 0.6 |
| total | 100% | 100% |
| calc. caloric density | 3.85 kcal/gm | 3.9 kcal/gm |

Using these diets supplemented by reference or unknown test substances fed as microencapsulated oils, sample body weight (hereinafter abbreviated "wgt") gains for example animals A and B fed corn oil as a reference (9.0 calories/gram) are as follows:

| diet supplied | Animal A wgt gain (grams) | Animal A calories consumed | Animal B wgt gain (grams) | Animal B calories consumed |
|---|---|---|---|---|
| ad lib AIN-76A | 73.6 | 1275 | 82.4 | 1370 |
| 50% fort | −3.4 | 651 | −3.8 | 691 |
| 50% fort + 7.75% gelatin | 9.0 | 705 | 8.3 | 747 |
| 50% fort + 7% corn oil | 13.9 | 768 | 15.2 | 831 |
| 50% fort + 14% corn oil | 28.3 | 913 | 37.9 | 998 |
| 50% fort + 21% corn oil | 57.7 | 1093 | 63.3 | 1183 |

Rats were fed a diet of 50% fort and 21% 1,1,1-trishydroxymethylethane trioleate prepared in Example 1 as a test compound under the foregoing procedure, and their weight gain was determined. Based upon the base line control data, and the data from the test compound, it was determined that 1,1,1-trishydroxymethylethane trioleate gave about 3.3 kcal/gram upon being metabolized.

EXAMPLE 11

In this example, a synthetic fat mimetic of this invention is used to prepare low calorie milk chocolate.

Equal parts of cocoa powder, sugar and the fat mimetic prepared in Example 7 are mixed in a glass beaker and are incubated with frequent stirring at 65° C. until a smooth, uniform fudge-like mixture is obtained. Lecithin, which is normally added at about 0.5% to chocolate and palm kernel oil to lower viscosity, is unnecessary since the viscosity of the fat mimetic is well suited to pouring into molds or enrobing. The hot mixture is poured into molds and quench cooled by placing in a freezer at approximately −10° C. No tempering regimen is necessary.

EXAMPLE 12

Filled Cream. About 18 Kg of a fat mimetic of Example 3 may be homogenized with 82 Kg of skim milk in a conventional dairy homogenizer to afford a "filled cream" composition.

EXAMPLE 13

Ice Cream. The "filled cream: composition of Example 12 (68 parts) may be combined with 15 parts condensed skim milk, 15 parts sugar, 0.5 parts gelatin, 1.0 part flavor, and 0.25 parts color to produce an ice cream mix which is processed in the normal manner to yield a modified ice cream product.

EXAMPLE 14

Filled Milk. About 100 parts of the filled cream composition prepared in Example 12 may be combined with about 620 parts of skim milk to prepare a "filled milk" composition.

EXAMPLE 15

Cheese Products. The filled milk product obtained in Example 14 may be treated like natural milk in the normal cheese making process (as is practiced, for example in the production of cheddar or swiss cheese). Preferably 10% butter oil is added to the fat mimetic portion of the filled milk product before it is employed in this process to enhance the proper flavor development of the cheese products.

EXAMPLE 16

Butter cream icing may be prepared by blending:

| Ingredient | g. |
|---|---|
| Sugar | 227.0 |
| Fat mimetic of Example 1 | 70.8 |
| Water | 28.4 |
| Non-Fat Dry Milk | 14.0 |
| Emulsifier | 1.4 |
| Salt | 1.0 |
| Vanilla | 1.0 |

All of the ingredients are creamed in a mixer at medium speed.

EXAMPLE 17

Vanilla Wafers. Twenty-five parts of a fat mimetic of Example 3 may be blended with 100 parts flour, 72 parts granulated sugar, 5 parts high fructose corn syrup, 1 part non-fat dry milk, 1 part salt, 1/10 part ammonium bicarbonate, 1 part dried egg yolk, 1/10 part sodium bicarbonate, and 55 parts water. The dough so formed may be rolled, wire cut to ¼ inch thickness, and baked by the usual process to give a vanilla wafer cookie.

EXAMPLE 18

Sprayed Crackers. A dough prepared from 100 parts flour, 5 parts sugar, 1.5 parts salt, 7.5 parts of the fat mimetic prepared in Example 3, 1 part salt, 0.9 parts sodium bicarbonate, 2.5 parts non-fat dry milk, 2.5 parts high fructose corn syrup, 0.75 parts mono calcium phosphate, and 28 parts water is sheeted, stamped, and baked to produce a cracker product.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention which is defined by the following claims.

What is claimed is:

1. A food composition comprising a partially digestible edible fat of the formula

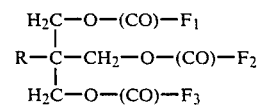

wherein R is a methyl or ethyl group, and $F_1$, $F_2$, and $F_3$ are the same or different fatty acid residues comprising from 10 to 22 carbon atoms.

2. The composition according to claim 1 wherein the fatty acid residues are selected from the group consisting of capric, undecanoic, lauric, myristic, palmitic, stearic, arachidic, behenic, oleic, linoleic, linolenic, eleostearic, and arachidonic acids, and mixtures thereof.

3. The composition according to claim 1 wherein the fatty acid residues comprise $C_{10}$ to $C_{20}$ fatty acid residues.

4. The composition according to claim 1 wherein fatty acid residues are selected from the group consisting of non-hydrogenated and hydrogenated sunflower, safflower, soybean, peanut, sesame, babassu nut, olive, canola, rice bran, coconut, palm kernel, palm, cottonseed, corn oil fatty acids and mixtures thereof.

5. The composition of claim 1 wherein the fatty acid residues comprise $C_{12}$ to $C_{18}$ fatty acid residues.

6. The composition of claim 1 wherein said food composition is a cookie.

7. The composition of claim 1 wherein said food composition is a biscuit.

8. The composition of claim 1 wherein said food composition comprises filled cream.

9. The composition of claim 8 wherein said filled cream further comprises skim milk.

10. The composition of claim 1 wherein said food composition comprises an ice cream mix.

11. The composition of claim 1 wherein said food composition is a cheese product.

12. The composition of claim 1 wherein said food composition is a vanilla wafer.

13. The composition of claim 1 wherein said food composition is a cracker dough.

14. The composition of claim 13, baked to produce a cracker product.

15. The composition of claim 1 wherein said food composition is a frozen dessert.

16. The composition of claim 1 wherein said food composition is selected from the group consisting of puddings and pie fillings.

17. The composition of claim 1 wherein said food composition is a margarine substitute.

18. The composition of claim 1 wherein said food product is selected from the group consisting of mayonnaise and salad dressing.

19. The composition of claim 1 wherein said food composition is a spread for breads or biscuits.

20. The composition of claim 1 wherein said food composition comprises a dairy product.

21. The composition of claim 1 wherein said food composition comprises a dairy substitute product.

22. The composition of claim 1 wherein said food composition comprises a meat substitute.

23. The composition of claim 1 wherein said food composition is selected from the group consisting of frosting and fillings.

24. The composition of claim 1 wherein said food composition is a candy.

25. The composition of claim 1 wherein said food composition is a bakery product.

26. The composition of claim 1 wherein said food composition comprising a mix for a bakery product.

27. A method of preparing a reduced calorie food composition which comprises formulating said composition with a partially digestible fat mimetic ingredient of the formula:

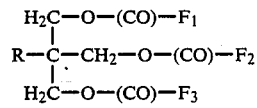

where R is a methyl or ethyl group and $F_1$, $F_2$, and $F_3$ are the same or different fatty acid residues comprising from 10 to 22 carbon atoms.

28. A partially digestible edible synthetic fat mimetic comprising trishydroxymethylethane trioleate.

29. A partially digestible edible synthetic fat mimetic comprising trishydroxymethylpropane trioleate.

30. A partially digestible edible synthetic fat mimetic comprising trishydroxymethylethane trimyristate.

31. A partially digestible edible synthetic fat mimetic comprising trishydroxymethylethane tristearate.

32. A partially digestible edible synthetic fat mimetic comprising trishydroxymethylethane tripalmitate.

33. A partially digestible edible synthetic fat mimetic comprising trishydroxymethylethane dioleate stearate.

34. A partially digestible edible synthetic fat mimetic comprising trishydroxymethylpropane trimyristate.

35. A partially digestible edible synthetic fat mimetic comprising trishydroxymethylpropane tristearate.

36. A partially digestible edible synthetic fat mimetic comprising trishydroxymethylpropane tripalmitate.

37. The method of claim 27 wherein said fatty acid residues have from ten to twenty carbon atoms.

38. The method of claim 37 wherein said fatty acid residues have from twelve to eighteen carbon atoms.

39. A method of preparing a reduced calorie food composition which comprises formulating said composition with a fat mimetic as defined in any of claims 28-36.

40. In a fat containing food composition the improvement wherein at least a portion of the digestible fat ingredient is replaced by a partially digestible fat mimetic of the formula

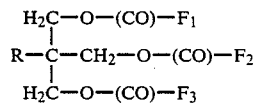

where
R is a methyl ($CH_3$—) or ethyl ($CH_3CH_2$—) group, and
$F_1$, $F_2$, and $F_3$ are $C_{10}$ to $C_{22}$ fatty acid residues.

41. The composition of claim 40 wherein the fatty acid residues are derived from mixtures comprising fatty acids having 10 to 20 carbon atoms.

42. The composition of claim 40 wherein the fatty acid residues are derived from fatty acids selected from the group consisting of capric, undecanoic, lauric, myristic, palmitic, stearic, arachidic, behenic, oleic, linoleic, linolenic, eleostearic, and arachidonic acids.

43. The composition of claim 40 wherein the fatty acid residues are selected from the group consisting non-hydrogenated and hydrogenated sunflower, safflower, soybean, olive, sesame, peanut, palm kernel, cottonseed, palm, babassu nut, canola, rice bran, and corn oil.

44. A method of preparing low calorie chocolate by mixing equal parts cocoa powder, sugar, and partially digestible trishydroxymethylethane trimyristate, stirring and incubating at 65° C. until a smooth, uniform mixture is obtained, placing the hot mixture into molds, and cooling.

45. A method of preparing low calorie filled cream by homogenizing partially digestible 1,1,1-trishydroxyethane dioleate/stearate with skim milk.

46. An edible composition comprising partially digestible trishydroxymethyl ethane esterified with fatty acids derived from mixtures comprising fatty acids having from 10 to 20 carbon atoms.

47. An edible composition comprising partially digestible trishydroxymethyl propane esterified with fatty acids derived from mixtures comprising fatty acids having from 10 to 20 carbon atoms.

48. The composition according to claims 46 or 47 wherein the fatty acids have from 12 to 18 carbon atoms.

* * * * *